US009918554B2

United States Patent
Song

(10) Patent No.: US 9,918,554 B2
(45) Date of Patent: Mar. 20, 2018

(54) FUNCTIONAL CHAIR FOR HUMAN BODY CORRECTION AND THERMAL THERAPY

(71) Applicant: Seong Jin Song, Daegu (KR)

(72) Inventor: Seong Jin Song, Daegu (KR)

( * ) Notice: Subject to any disclaimer, the term of this patent is extended or adjusted under 35 U.S.C. 154(b) by 103 days.

(21) Appl. No.: 15/034,707

(22) PCT Filed: Oct. 15, 2014

(86) PCT No.: PCT/KR2014/009654
§ 371 (c)(1),
(2) Date: May 5, 2016

(87) PCT Pub. No.: WO2015/076499
PCT Pub. Date: May 28, 2015

(65) Prior Publication Data
US 2016/0262544 A1 Sep. 15, 2016

(30) Foreign Application Priority Data
Nov. 19, 2013 (KR) ........................ 10-2013-0140619

(51) Int. Cl.
*A47C 7/72* (2006.01)
*A47C 7/74* (2006.01)
(Continued)

(52) U.S. Cl.
CPC .............. *A47C 7/748* (2013.01); *A47C 3/16* (2013.01); *A47C 7/021* (2013.01); *A47C 7/16* (2013.01);
(Continued)

(58) Field of Classification Search
CPC ...... B60N 2/56; B60N 2/5607; B60N 2/5685; B60N 2/5692; F28D 15/00; A47C 7/748;
(Continued)

(56) References Cited

U.S. PATENT DOCUMENTS 3,136,577 A * 6/1964 Richard ............... B60N 2/5692
219/202
5,516,189 A * 5/1996 Ligeras ................. A47C 7/748
219/202
(Continued)

FOREIGN PATENT DOCUMENTS

JP 2004-344490 A 12/2004
JP 3118765 U9 1/2006
(Continued)

*Primary Examiner* — Chi Q Nguyen
(74) *Attorney, Agent, or Firm* — Novick, Kim & Lee, PLLC; Jae Youn Kim

(57) ABSTRACT

The present disclosure relates to a functional chair for human body correction and therapeutic efficacy promotion by applying heat, including: a main body which includes a sitting plate and a waist plate; a heating means to transfer the heat to a human body by using a ceramic heating element installed in the sitting plate and the waist plate; and a control unit which maintains the temperature of the heating means at a pre-established value and displays an operating status. The present disclosure provides immunity increase and health promotion by keeping a skeletal structure and organs balanced by allowing a user to keep a correct posture when they are sitting on the functional chair and by applying heat to a structure including the sitting and waist plates as a Korean traditional floor heating system, which has no influence of electromagnetic waves, does, provides convenience of portability and performs therapeutic effects for various body parts including the vertebral column, calves, feet, etc.

5 Claims, 9 Drawing Sheets

(51) Int. Cl.
- *A61F 7/03* (2006.01)
- *A47C 3/16* (2006.01)
- *A47C 7/02* (2006.01)
- *A47C 16/02* (2006.01)
- *A47C 7/16* (2006.01)
- *A47C 7/46* (2006.01)
- *A61F 7/08* (2006.01)
- *A61F 7/00* (2006.01)
- *A61H 37/00* (2006.01)

(52) U.S. Cl.
CPC ............... *A47C 7/46* (2013.01); *A47C 16/02* (2013.01); *A61F 7/03* (2013.01); *A61F 7/08* (2013.01); *A61F 2007/004* (2013.01); *A61F 2007/0023* (2013.01); *A61F 2007/0027* (2013.01); *A61F 2007/0043* (2013.01); *A61F 2007/0045* (2013.01); *A61F 2007/0047* (2013.01); *A61H 37/00* (2013.01); *A61H 2201/0207* (2013.01)

(58) Field of Classification Search
CPC .... A47C 7/46; A47C 7/16; A47C 3/16; A47C 7/021; A47C 16/02; A61F 7/08; A61F 7/03; A61F 2007/0023; A61F 2007/0027; A61F 2007/004; A61F 2007/0043; A61F 2007/0045; A61F 2007/0047
USPC ..... 297/180.1, 180.12, 180.11, 217.1, 217.3; 62/3.2, 3.5
See application file for complete search history.

(56) References Cited

U.S. PATENT DOCUMENTS

| | | | | |
|---|---|---|---|---|
| 5,924,767 | A * | 7/1999 | Pietryga | A47C 7/74 297/180.11 |
| 6,302,094 | B1 * | 10/2001 | Wehrly | A47C 7/744 126/204 |
| 7,741,582 | B2 * | 6/2010 | Howick | B60N 2/5678 219/202 |
| 7,866,743 | B1 * | 1/2011 | Russell | A47C 7/74 297/180.1 |
| 8,492,680 | B2 * | 7/2013 | Ohashi | B60N 2/5685 219/202 |
| 9,139,119 | B2 * | 9/2015 | Ohashi | B60N 2/5685 |
| 2005/0161985 | A1 * | 7/2005 | Austin | A47C 7/748 297/180.12 |
| 2006/0130490 | A1 * | 6/2006 | Petrovski | A47C 7/74 62/3.3 |
| 2008/0087316 | A1 * | 4/2008 | Inaba | B60N 2/5692 136/204 |
| 2009/0032158 | A1 * | 2/2009 | Rudolf | B60C 23/003 152/415 |
| 2009/0033130 | A1 * | 2/2009 | Marquette | A47C 7/74 297/180.15 |

FOREIGN PATENT DOCUMENTS

| | | |
|---|---|---|
| KR | 20-1996-0009822 U | 4/1996 |
| KR | 10-1999-0064481 A | 8/1999 |
| KR | 20-0153954 Y1 | 8/1999 |
| KR | 10-1023973 B1 | 3/2011 |

\* cited by examiner

FUNCTIONAL CHAIR FOR HUMAN BODY CORRECTION AND THERMAL THERAPY

BACKGROUND OF THE DISCLOSURE

1. Field of the Disclosure

The present disclosure relates to a chair for both human body correction and thermal therapy, and more particularly, to a functional chair for providing human body correction together with thermal therapy which keeps a skeletal structure and organs balanced by allowing a user to keep a correct posture when they sitting on the functional chair and by applying heat as a Korean traditional floor heating system does.

2. Description of the Related Art

Modern people, who live in an age of extreme competition, spend a lot of time in sitting in front of a desk in their house or office or on various chairs or couches, which may cause, due to an improper posture, vertebral, cervical and lumbar deformities and incur, due to a variety of chronic incurable diseases, a considerable burden of medical expenses as they get older. Moreover, when they spend excessive money for purchasing and maintaining an apparatus or a medical device to resolve such problems, they should additionally bear another economic burden on top of loss of time spent for a treatment. Therefore, although countless attempts have been continued to correct a deformed part by selecting various techniques including massage therapy, the thermal therapy, far infrared ray radiation, rubdown/acupressure therapy, traction therapy, etc. or promote convenience of correction of treatments by applying a method such as thermal therapy to a chair, it still falls under a very serious problem to overcome. In terms of prior art, Korean Patent Publication No. 1999-0064481, Korean Patent Registration No. 1023973, etc. have been disclosed.

The former prior patent relates to a chair equipped with a leg-cum-support, a seat, a back, a headrest and an angle adjustment means, wherein a thermal therapeutic apparatus, which has a far infrared ray radiating lamp installed in the lower portion of a pressing protuberance inside a body of the chair, is directly buried in the back of the chair so that the thermal therapeutic apparatus can adhere to and be removed from the front of the back. Therefore it is expected that chair usability would be promoted and that the former prior patent would contribute to user health.

The latter prior patent relates to a thermal massaging floor chair which has a thermal massaging unit which protrudes, a perineum front and rear ends massaging rod which is buried inside the thermal massaging floor chair, and, outside the thermal massaging floor chair, a sitting plate inserting unit and a back plate inserting unit, wherein the central rear end of a sitting plate is connected to the central rear end of a back by means of an elastomer. Therefore, by applying a thermal effect to and massaging the perineum as the thermal massaging unit operates, it is expected that the thermal massaging floor chair may prevent and treat a prostate gland disease and urinary incontinence.

However, although the former prior patent has an effect of far infrared ray therapy and the latter prior patent is capable of reinforcing a specific body part, both prior patents are relatively very insufficient to perform a function of correcting a human body and have a remarkable influence of electromagnetic waves when heating.

SUMMARY OF THE DISCLOSURE

In order to resolve the problems inherent to the prior art, the present disclosure provides a functional chair for providing not only human body correction and posture correction which keep a skeletal structure and organs balanced but also thermal therapy by allowing a user to keep a correct posture when they are sitting on the functional chair and by applying heat to a structure including a sitting plate and a waist plate as a Korean traditional floor heating system, which has no influence of electromagnetic waves, does. To allow a chair to keep a correct posture when the user is sitting on the chair, the chair should have a structure that keeps a lumbar vertebra, which is the most vulnerable point in a central skeletal structure which comprises the head, vertebra column (cervical, thoracic and lumbar) and pelvis, of a human being, which is the only orthograde one among countless animals, correct and maintains the pelvis properly balanced when they walk, under which the functional chair according to the present disclosure should fall. Another major one among the objectives of the present disclosure is a simple structure for securing convenience of portability with a therapeutic efficacy for various parts including a calf, a foot, etc. along with the vertebra.

In order to achieve the objectives, the functional chair which corrects a human body and promotes the therapeutic efficacy by applying the heat includes:

a main body which includes the sitting plate and the waist plate;

a heating means to transfer the heat to the human body by means of a ceramic heating element installed in the sitting plate and the waist plate; and a display unit which maintains the temperature of the heating means at a preestablished value and displays an operating status.

The sitting plate includes a plateau unit which protrudes from the central area and a circuit board installed and buried in front of the plateau unit while the waist plate includes a curved surface unit with a specific curvature.

In addition, the main body includes at least one among an angle adjusting unit which adjusts the angle of the waist plate, an up-and-down adjusting unit which adjusts the height of the waist plate and a leg unit which adjusts the height of the sitting plate.

Also in addition, the heating means includes a protective pad in the top portion and the bottom portion of the ceramic heating element, lagging into which vermiculite and silica are mixed above and beneath the ceramic heating element and an insulator beneath the lagging.

Terms and words specified in the present specification and claims therein must not be determined or interpreted either in a conventional way or word for word but be interpreted as a sense and a concept which accord with the technical thoughts of the present disclosure following the principle that the inventor may appropriately define the concept of the terms in order to explain their invention in the best way. Accordingly, one should understand, because embodiments specified in the present specification and configurations described in the drawings are nothing more than the most preferable ones according to the present disclosure and do not wholly represent the technical thoughts of the present disclosure, there may be, at the time of filing the present disclosure, a plurality of equivalents and modified examples which can replace the embodiments and configurations.

The present disclosure has advantageous effects of correcting the skeletal structure and posture and keeping the organs balanced, thereby organically promoting health by allowing a user to keep a correct posture when they are sitting on the functional chair which includes the ceramic heating element installed the sitting plate and the waist plate and by applying the heat as a Korean traditional floor heating system, which has no influence of electromagnetic waves, does.

DETAILED DESCRIPTION OF THE EMBODIMENTS

Figure 1:
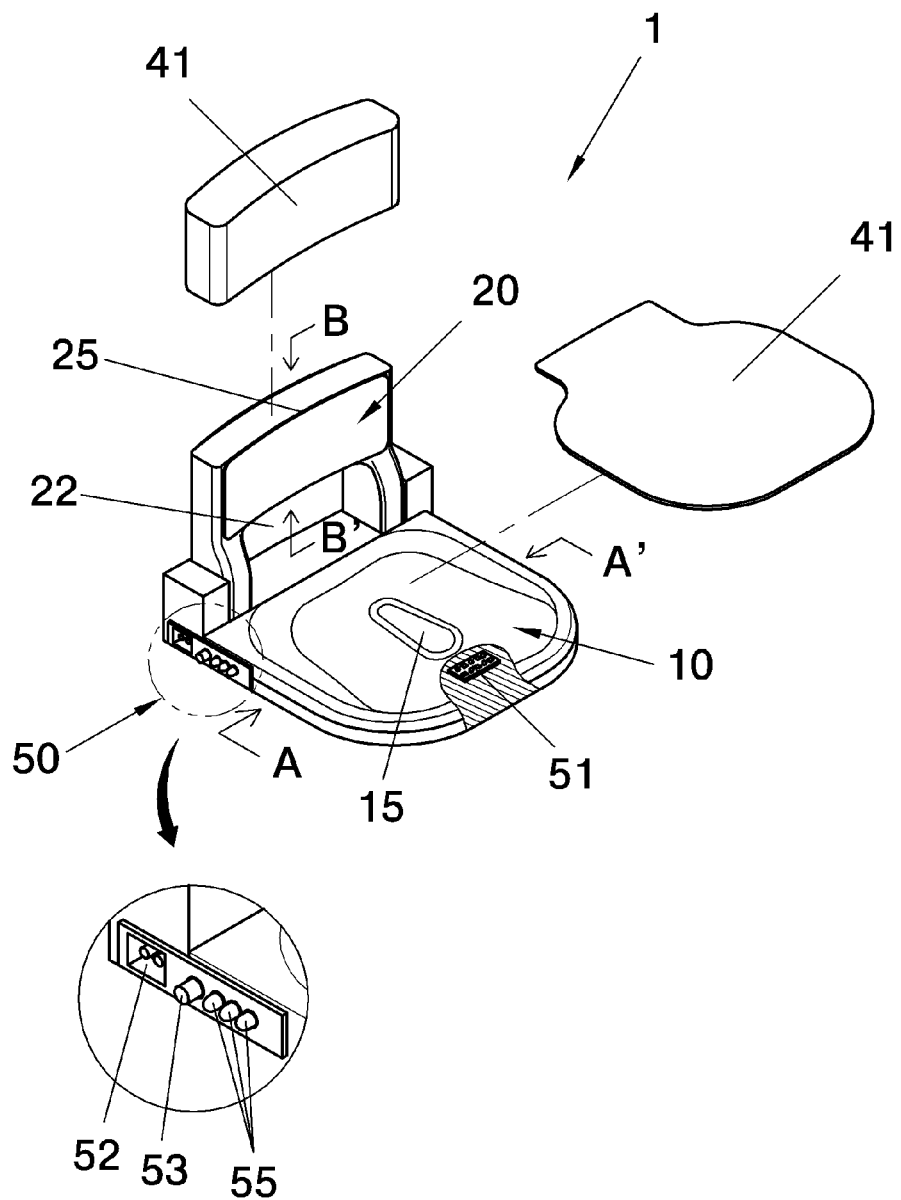
FIG. 1 is a general configuration drawing of the chair according to an embodiment of the present disclosure.

Embodiments of the present disclosure will be now described in detail with reference to the drawings attached.

The present disclosure proposes a chair for human body correction and treatment efficacy promotion by using heat. A human vertebral column is composed of 24 bones including 7 cervical vertebrae, 12 thoracic vertebrae and 5 lumbar vertebrae. The vertebral column has excellent side-to-side and up-and-down flexibility because the head is placed over the cervical vertebrae. The thoracic vertebrae have little side-to-side flexibility because they are connected to the sternum right in the middle of the chest and ribs and up-and-down flexibility also considerably lower than that of the cervical and lumbar vertebrae. The lumbar vertebrae are placed above the sacrum, which is a large bone like a pedestal as a mass of 5 sacral vertebrae, and have excellent side-to-side and up-and-down flexibility although they support the weight of the head, cervical vertebrae and thoracic vertebrae. The thoracic vertebrae have no flexibility but are firm whereas the cervical and lumbar vertebrae have less rigidity, thereby being vulnerable to deformities and damage although they have excellent flexibility. The lumbar vertebrae are more vulnerable to deformities than the cervical vertebrae because they should exert the largest strength in all activities including sitting down, getting up and lifting up an object because the lumbar vertebrae are placed over the sacrum, the large bone like a pedestal, support the weight of the head, cervical vertebrae and lumbar vertebrae and are placed in the center of a human body. The most vulnerable ones among the 5 lumbar vertebrae are Nos. 4 and 5 which are placed in the bottom, where lumbar herniated intervertebral disc, also called prolapsed disc, most frequently occurs. Therefore, considering such an aspect, the present disclosure relates to the chair for human body correction and treatment efficacy promotion, wherein a main body includes a waist plate 20 and a sitting plate 10.

Correcting every skeletal structure and organ position starts with vertebral correction. The vertebral correction starts with correction of the lumbar vertebrae and pelvis while various kinds of therapeutic exercise including sitting up straight to correct the vertebral column focus on keeping the lumbar vertebrae and pelvis correct.

A common chair focuses on its back that supports, instead of the lumbar vertebrae, the thoracic vertebrae. However, the present disclosure has removed a back section and provides the waist plate only following a human body principle that the thoracic vertebrae spread straight as long as the lumbar vertebrae spread straight. In addition, such a common chair has a soft material to finish its sitting plate to reduce a sore part around the pelvis, which may set the pelvis distorted. On the other hand, the present disclosure employs a material which reduces softness of the sitting plate to the extent possible so that the deformed pelvis returns to its correct position when a user is sitting on the chair. The pain the user senses when the deformed pelvis returns to its correct position is considerably mitigated by heat radiated by a configuration of the chair which is similar to a Korean traditional floor heating system.

The waist plate 20 is combined with a side of the sitting plate 10, wherein a space section 22 may be formed in the lower portion of, where the waist plate is connected to the sitting plate 10, of the waist plate 20. The sacrum, below which the coccyx is connected, which supports the lumbar vertebrae is placed in the space section 22. The sacrum, which is a large bone, belongs, in a broad sense, to the pelvis and is very strong. It causes no problem to place the sacrum in the space section 22 in that the sacrum experiences nearly no deformities and requires nearly no heating. Therefore, the space section can be used as space through which the ankles are placed in order to heat the calves on the sitting plate as illustrated in FIG. 4C.

According to a detailed configuration of the present disclosure, the sitting plate 10 has a plateau unit 15 that protrudes from the central area and a circuit board 51 is installed and buried in the sitting plate 10 in front of the plateau unit 15 while the waist plate 20 has a curved surface area 25 with a specific curvature. The plateau unit 15 of the sitting plate 10 is placed at a place corresponding to the perineal acupuncture point at which the two streams of a yin energy which rise from the ground via the feet in order to flow energies and blood of the entire body. Needless to say, the plateau unit 15 can be formed differently in terms of the shape and size for each of the chairs for men and women, respectively. Although it is preferable to install the circuit board 51 which is buried inside the sitting plate 10, in front of the plateau unit 15, the plateau unit may be installed in another place. In other words, the circuit board can be designed to be arranged besides a control unit 50 on a side of the sitting plate 10 or located at the front, to the left, to the right, at the rear, etc. of the plateau unit 15. It would cause no problem to integrate the circuit board 51 with the control unit 50 into one piece because the circuit board 50 only has to be integrated, to well operate, with the control unit 50. It should be pointed out that the specific curvature does not mean only a single value because the curved surface unit assumes a shape as if the curved surface unit enfolds the waist.

Figure 3A:
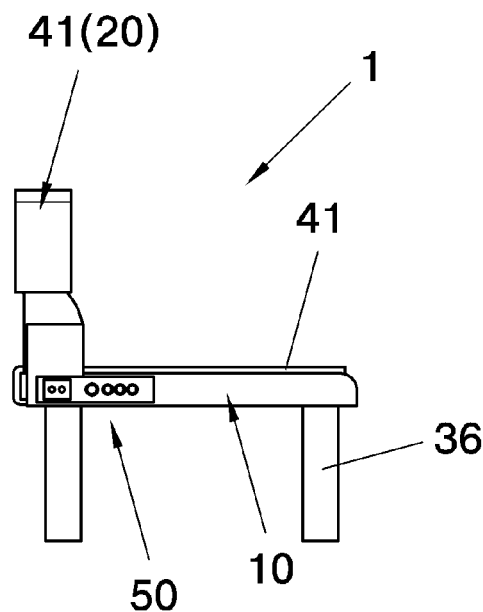
FIG. 3A is a configuration drawing which illustrates the chair equipped with a short leg unit according to an embodiment of the present disclosure.
Figure 3B:
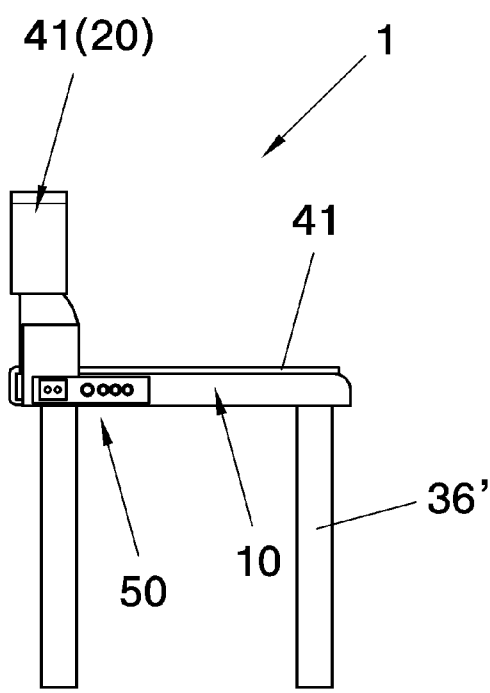
FIG. 3B is a configuration drawing which illustrates the chair equipped with a long leg unit according to an embodiment of the present disclosure.

According to another detailed configuration of the present disclosure, the main body includes at least one among an angle adjusting unit 32 which adjusts the angle of the waist plate 20, an up-and-down adjusting unit 34 which adjusts the height of the waist plate 20 and a leg unit 36, 36' which adjusts the height of the sitting plate. The angle adjusting unit 32 is installed in order to adjust the angle of the waist plate 20 relative to the sitting plate 10 around from 90 to 120°, to which a known technology may be applied. Although not being illustrated in the drawings, the angle adjusting unit 32 may employ a worm wheel connected to a hinge axis and a worm gear having a nob in order to simply the configuration. The up-and-down adjusting unit 34 is installed in order to adjust the height of the waist plate 20 relatively to the sitting plate 10 depending on the size of the user, to which a known technology may also be applied. The leg unit 36, 36' can adjust the height of the sitting plate 10 relative to the ground as selected by the user. (Refer to FIGS. 3A and 3B.) The chair in FIG. 1 has no leg unit whereas the chairs in FIGS. 3A and 3B have the separate leg units 36, 36' although the leg length of each of the leg units is different from each other. As a result, the chair in FIG. 1 can be used on a common chair, a couch or the ground whereas the chair which has the leg unit as illustrated in FIGS. 3A and 3B can be used as if the chair is per se a common chair. So as to simplify the configuration, each of the up-and-down adjusting unit 34 and the leg unit 36, 36' can be installed with a bolt which has a nob. According to the present disclosure, a heating means 40 transfers to the body heat by means of a ceramic heating element 45 installed in the sitting plate 10 and the waist plate 20. (A configuration A-A' in FIG. 1 corresponds to the heating means 40 and B-B' in FIG. 1 is a same configuration as A-A'.) The ceramic heating element 45 applies the heat by using electricity. However, the present disclosure shuts off the electricity upon starting to operate the chair and implements a treatment by using the heat stored. The heat can be maintained around from 40 to 80° for around 1 to 3 hours. The ceramic heating element 45, which is installed in the sitting plate 10 and the waist plate 20, may have a different specification, or wattage.

According to a detailed configuration of the present disclosure, the heating means 40 includes a protective pad 41 in the top portion and the bottom portion of the ceramic heating element 45, lagging 43 and an insulator 42 consecutively beneath the ceramic heating element 45 and the lagging 43 above the ceramic heating element 45. (Refer to FIG. 2A.) It is required that the protective pad 41 should have strength and wear resistance so as to resist the weight of the user and the protective pad may be made of one among an aluminum alloy plate, a copper plate, wood and high-strength resin. The insulator 42 beneath the ceramic heating element is to prevent the heat of the ceramic heating element 45 from being dissipated downward or to the ground or preserve the heat and made of one among a nonflammable fiber, foam resin, foam ceramics, etc. Although It is preferable, in a structural aspect, to mix 22 to 45% of kaolin, 15 to 35% of clay, 5 to 15% of agalmatolite, 5 to 15% of feldspar, 5 to 15% of silica, 2 to 10% of alumina, 2 to 10% of serpentine, etc., the components can be replaced with other materials which have characteristics equivalent to those of the components or one or two among the components can be omitted. However, it would be preferable to inevitably include the kaolin, clay, agalmatolite, feldspar, alumina or else. It is preferable to form a heating plate, which is an important component of the ceramic heating element 45, into a shape of a stone slab by using a ceramic material. A coil- or pipe-shaped heating element 44 is inserted in the ceramic heating element 45, wherein two or a plurality of the ceramic heating plates are stacked or attached to each other so that the heating plates are in proximity to each other. The insulator 43 is made of vermiculite and the silica with a mixing ratio of about 7 to 3, wherein the insulator 43 is formed into a light porous material in which a considerable number of pores are formed. A far infrared ray radiating material member 46 is inserted in the uppermost protective pad 41 or across the inside of the upper lagging 43 and the protective pad 41 and made of one among barley stone, germanium, titanium dioxide, silver, tourmaline, zeolite, the feldspar, the serpentine, the silica, etc. or a mixture of some thereof. Although the far infrared ray radiating material member doesn't have to be inserted, it might be said that the far infrared ray radiating material member would, when additionally inserted, have a far infrared ray or negative ions radiating effect to a more significant extent.

Figure 2A:
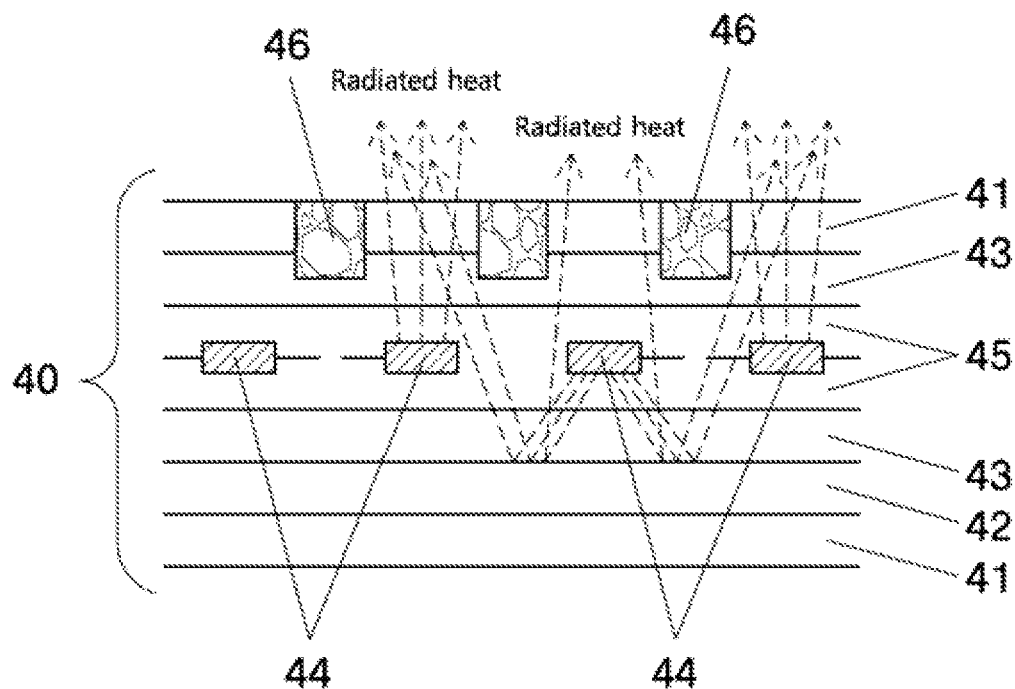
FIG. 2A is a cross-sectional view at A-A' (or B-B') of the heating means of the sitting plate of the chair according to an embodiment of the present disclosure.
Figure 2B:
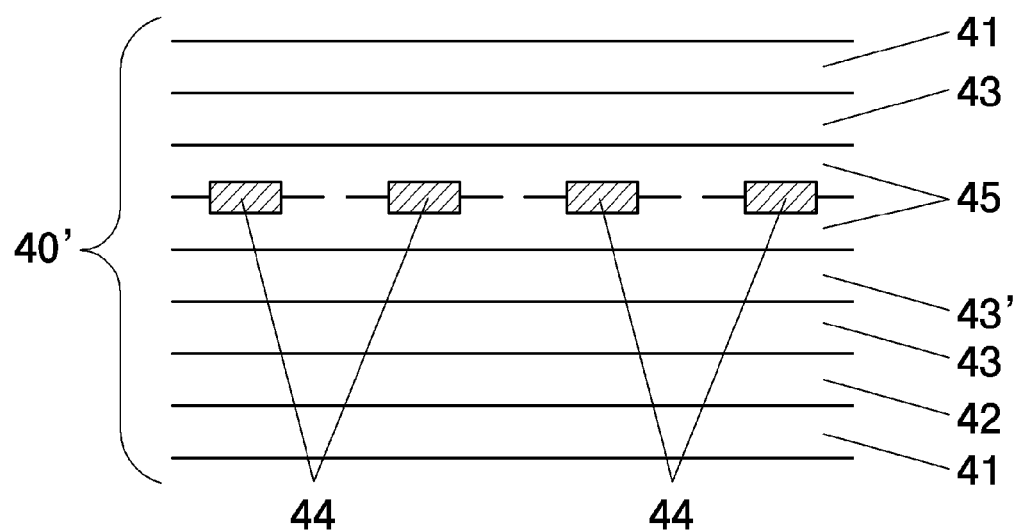
FIG. 2B is a cross-sectional view at A-A' (or B-B') of the heating means of the sitting plate of the chair according to another embodiment of the present disclosure.

The heating means 40' shown in FIG. 2B is an exemplary configuration for which some elements of the heating means 40 in FIG. 2A have been removed or to which other elements have been attached. More specifically, provided that the heating means 40, 40' according to the present disclosure inevitably includes the ceramic heating element 45 which includes the heating element 44, the configuration describes a fact that the lagging 42 or the insulator 43 can be added or omitted so as to preserve the heat of the ceramic heating element 45 and focus and radiate the heat upward, instead of downward. In other words, the heating means 40' in FIG. 2B has a stack configuration in which two layers of the lagging 43, 43' are stacked above the insulator 42 so that the heat of the ceramic heating element 45 is better preserved in the lower portion and dissipated upward for a longer time. Such a stacking configuration is nothing more than an example which can be easily modified and treated.

The control unit 50 according to the present disclosure has a configuration to maintain the temperature of the heating means 40 at a preestablished value and display an operating status. The control unit includes an electric wire input unit 52, or a socket unit, an operating switch 53 which is closed integrated with the circuit board 51 installed inside the sitting plate 10 and starts and stops an operation and a display device 55 which displays the operating status. The control unit 50 may be installed on a side of an armrest unit on a flank side of the sitting plate 10 or at any other place. The circuit board 51 is a microcomputer circuit in which a control algorithm is embedded and can convert domestic AC power into DC working power. The operating switch 53 inputs an independent operation into the sitting plate 10 and the waist plate 20 and can input simultaneous operations. The display device 55 displays a status related to the working temperature, working time, etc. of the ceramic heating element 45.

As to the operation, when an operating mode is selected and input via the operating switch 53 of the control unit 50, the ceramic heating element 45 is heated by means of the heating element 44 for about 3 to 10 minutes, after which the temperature of the ceramic heating element 45 exceeds about 100 to 250° C. In spite of the high temperature over about 200° C. at the ceramic heating element 45, the upper and lower pieces of the lagging 43 keep the heat at a lower temperature and dissipate the heat toward the protective pad 41 above the ceramic heating element, wherein the temperature of the surface which comes in contact with the upper protective pad 41 reaches about 60 to 80° C. The surface slowly cools down below 60° C. after about 90 to 120 minutes. When the surface cools down to a certain extent, the user can make the operating switch 53. Although the fluctuation range of the temperature of the ceramic heating element 45 or the heat transferred to the uppermost protective pad 41 may be adjusted as much as the user desires, it is preferred to establish the temperature of a part which comes in contact with the human body to be maintained at about 60 to 80° C. because a temperature over 80 to 90° C. which is transferred via the uppermost protective pad 41 can cause a burn. When the operating switch 53 is broken and the user sits on the chair by using the sitting plate 10 and the waist plate 20, warmth of the ceramic heating element 45 is continuously transferred to the human body for 60 to 180 minutes. It is needless to say that the period of time to heat transfer can be extended up to about 300 to 400 minutes in summer when ambient temperature is high or with a separate insulator such as blankets.

Figure 4A:
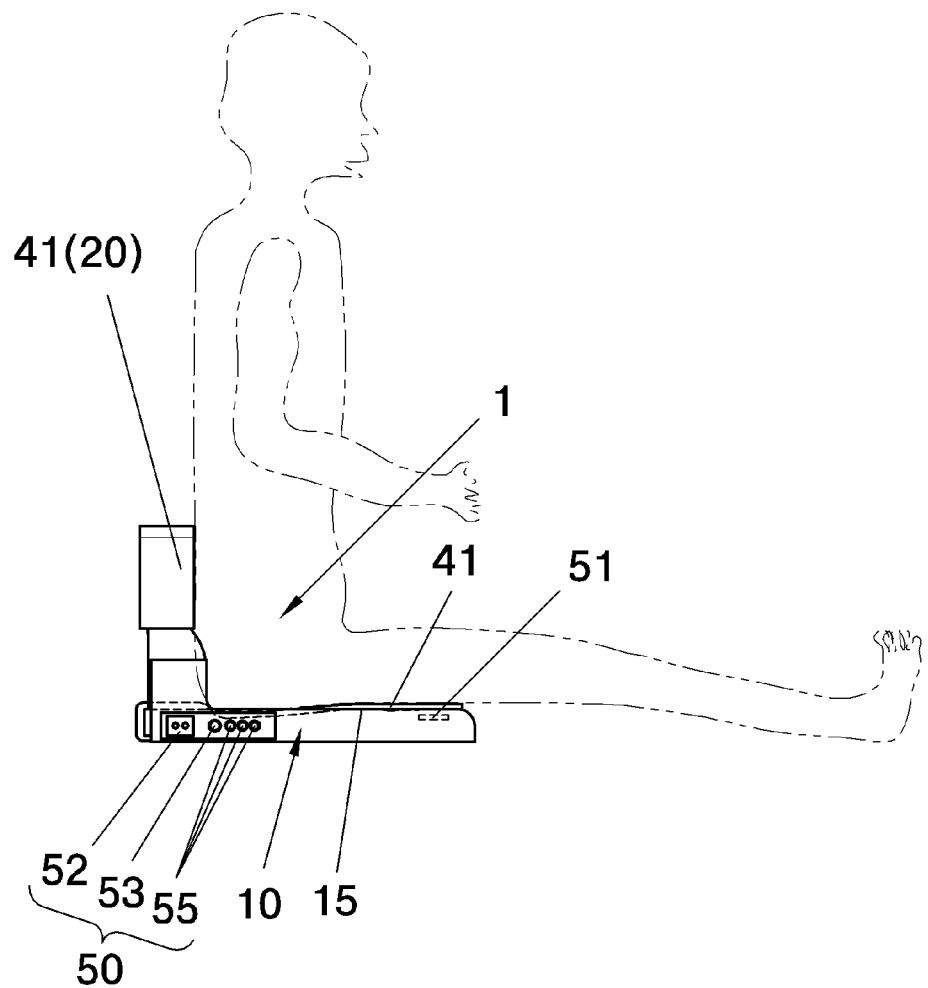
FIG. 4A illustrates a state of an embodiment of the present disclosure wherein the chair of FIG. 1 is laid down on a floor and used.
Figure 4B:
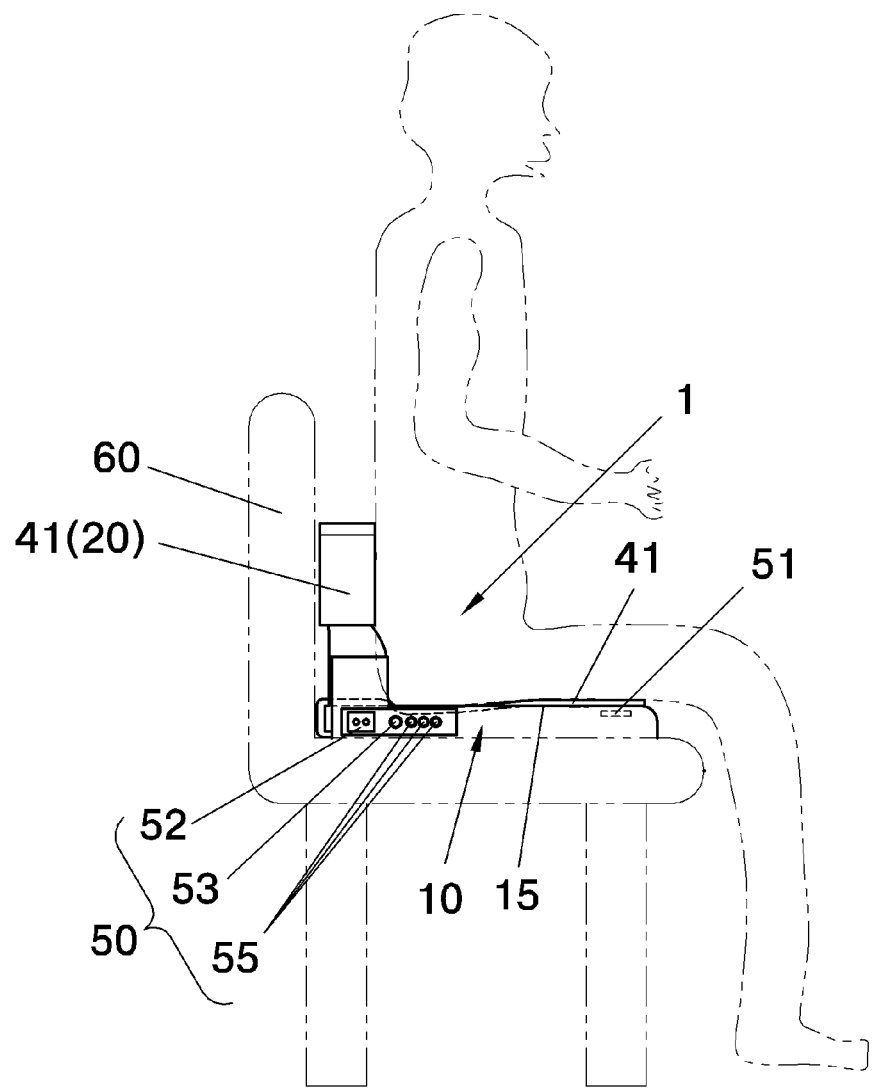
FIG. 4B is a state of an embodiment of the present disclosure wherein the chair of FIG. 1 is placed on a common chair and used.
Figure 4C:
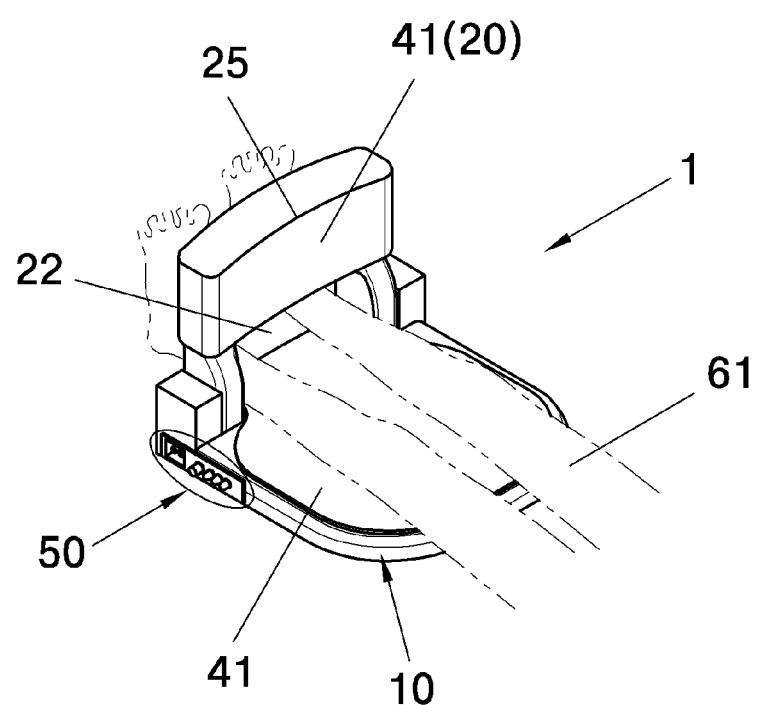
FIG. 4C is a state of an embodiment of the present disclosure wherein legs are placed inside and through the waist plate of the chair of FIG. 1.
Figure 4D:
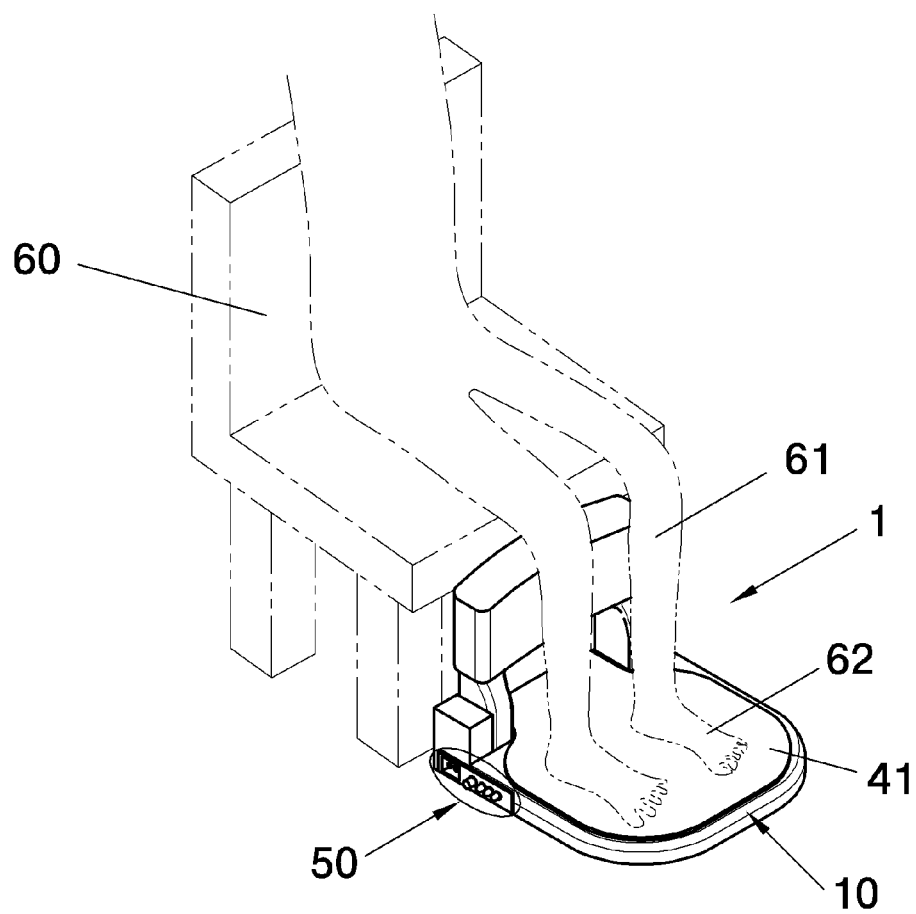
FIG. 4D is a state of an embodiment of the present disclosure wherein a user who sits on a common chair lays the chair of FIG. 1 down on a floor and uses the chair of FIG. 1.

As illustrated in FIG. 4A, the user can install the chair of FIG. 1 on the floor of a living room or a bedroom, sit thereon and fully extend their legs to watch TV or read a book in a most comfortable and straight posture. As illustrated in FIG. 4B, the user can lay the chair of FIG. 1 over a common chair and comfortably sit thereon for therapeutic activities or heat absorption. As illustrated in FIG. 4C, the user can insert their legs through the space section 22 of the waist unit 20 and lay their calves on the sitting plate 10 to treat their varicose vein, etc. As illustrated in FIG. 4D, the user also can receive thermal massage therapy sitting on another common chair and laying their feet on the sitting plate 10.

Figure 5A:
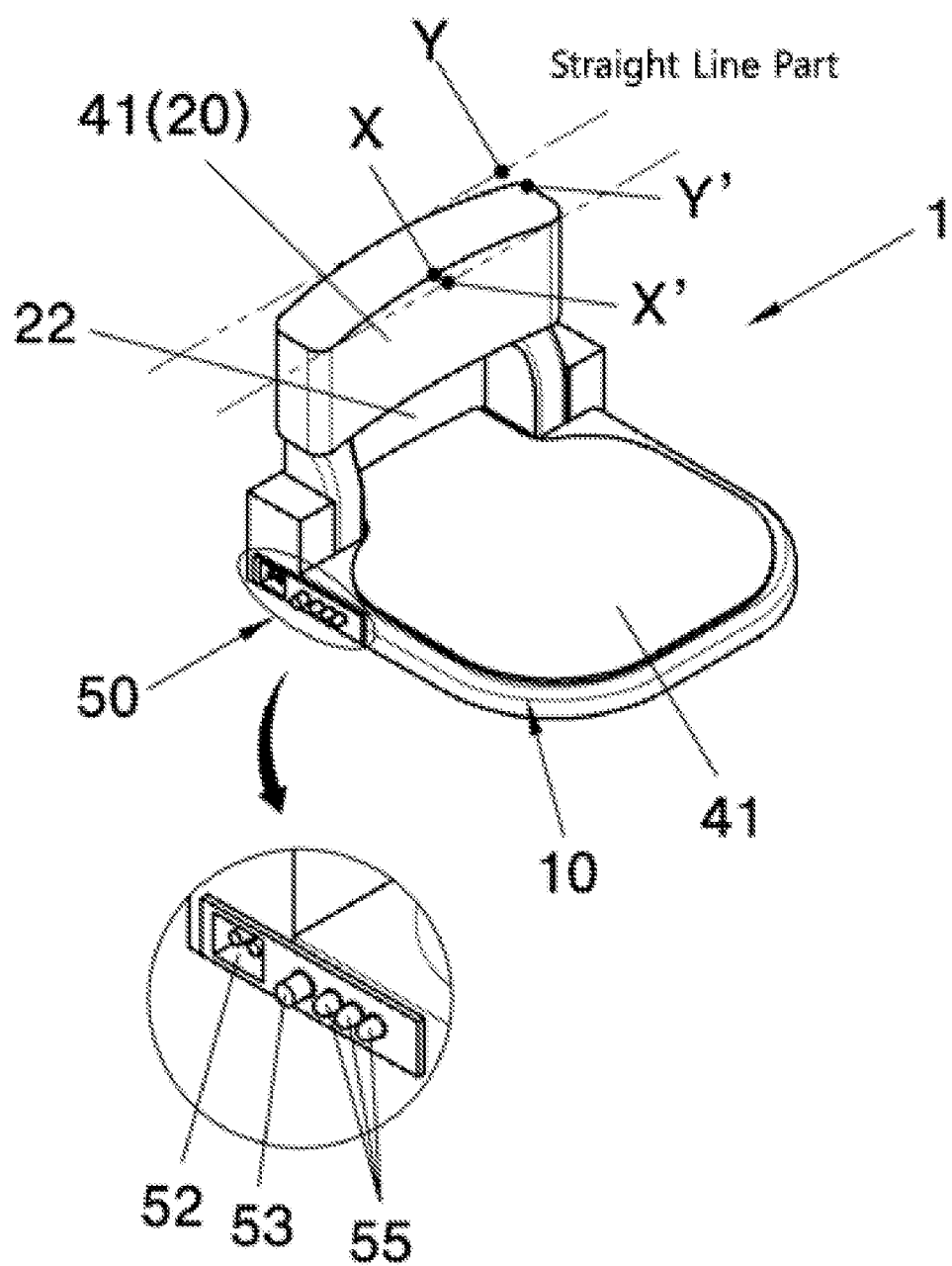
FIG. 5A is a configuration drawing which illustrates the curvature of the waist plate of the chair according to an embodiment of the present disclosure.

FIG. 5A shows the curvature of the waist plate 20. The curved section softly enfolds the waist for the ceramic heating element 45 to focus the heat on the lumbar vertebrae Nos. 4 and 5 so that more warmth is absorbed. More specifically, when the curved surface across X-X' (or Y-Y') as illustrated in FIG. 5A is formed into a curved surface optimized considering an ergonomic aspect, the efficacy of thermal therapy increases.

Figure 5B:
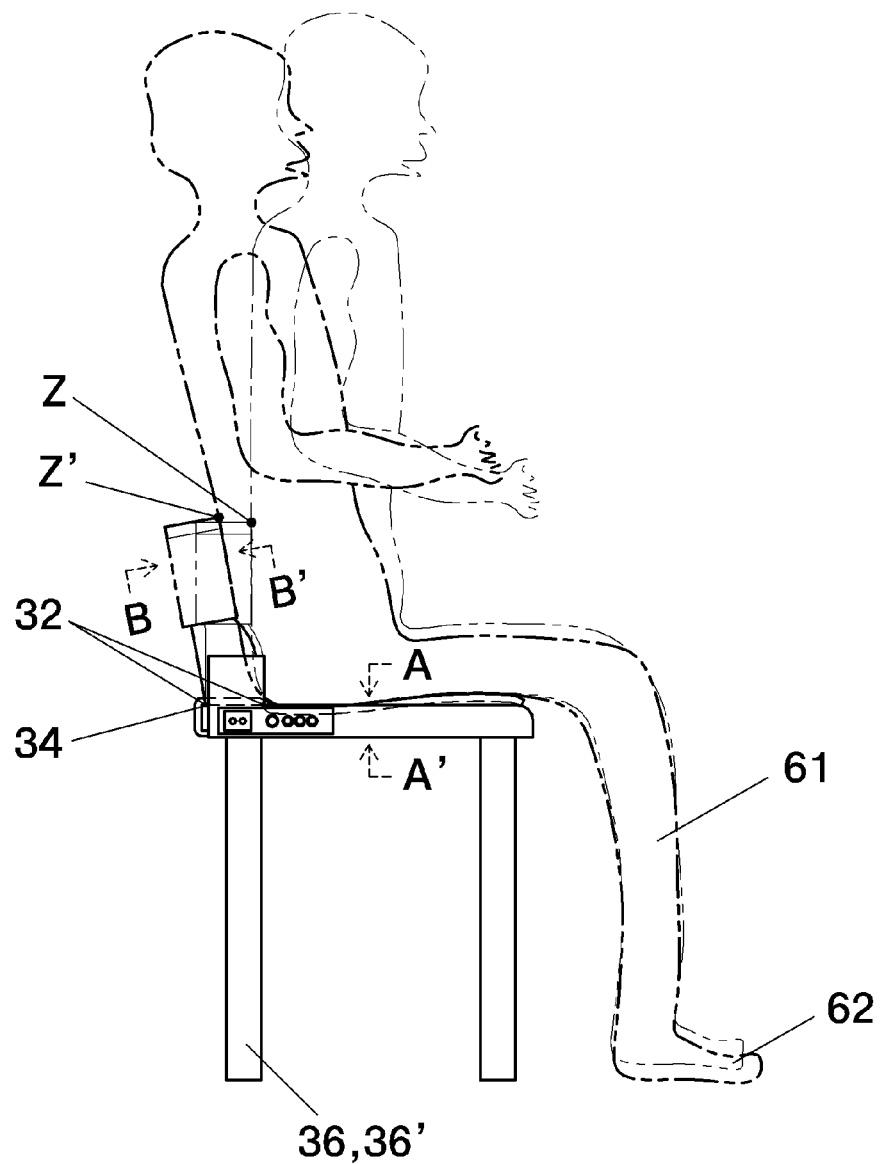
FIG. 5B is a configuration drawing which illustrates a state of the angle of the waist plate of the chair according to an embodiment of the present disclosure.

FIG. 5B illustrates the waist plate 20 tilted backward by about 110° from a perpendicularly upright position. Sitting up straight with the waist plate 20 upright to about 90 to 95° refers to a basic correction posture. However, sitting up straight, considering a distorted posture, with the waist plate further tilted by about 5 to 10° may allow the waist plate to mostly come in contact with the lumbar vertebrae Nos. 4 and 5 which are vulnerable to the prolapsed disc, increase the therapeutic efficacy and absorb the heat for a longer time in a comfortable posture.

The chair in FIG. 5B is exactly the same in a configurational aspect as that of the chair in FIG. 1 (cross-sectional structure across A-A' and B-B', control unit, etc.). The fact that attaching the leg unit 36, 36' to the chair in FIG. 1 enables the chair to be used the common chair is the only difference.

Reference characters 60, 61 and 62, which have not been described in the specification, refer to the common chair, the legs and the feet, respectively.

When the user sits on the functional chair, which employs a technique to use the heat stored in the ceramic heating element 45, according to the present disclosure, their body temperature increases even only by heating the perineal acupuncture point via the plateau unit 15 of the sitting plate 10, thereby remarkably reinforcing their immunity. Moreover, the present disclosure has significant effects of treating the impaired lumbar vertebrae, preventing prostate gland diseases, feeling of cold, leukorrhea, hemorrhoid, etc. and totally avoid hazards including electromagnetic waves, etc.

It is obvious to a person skilled in the art that the present disclosure must not be limited to the embodiments described thus far but may be modified and changed in various ways within the technical thoughts of the present disclosure. Therefore, such a modified or changed example should fall under the scope of the claims of the present disclosure.

REFERENCE CHARACTERS

10: Sitting plate
15: Plateau unit
20: Waist plate
22: Space section
25: Curved surface unit
32: Angle adjusting unit
34: Up-and-down adjusting unit
36, 36': Leg unit
40, 40': Heating means
41: Protective pad
42: Lagging
43: Insulator
44: Heating element
45: Ceramic heating element
46: Far infrared ray radiating material member
50: Control unit
51: Circuit board
52: Electric wire input unit (Socket unit)
53: Operating switch
55: Display device

What is claimed is:

1. A functional chair for human body correction and therapeutic efficacy promotion by applying heat, comprising:
   a main body which includes a sitting plate and a waist plate;
   a heating means configured to transfer the heat to a human body and including a ceramic heating element installed in the sitting plate and the waist plate; and
   a control unit which maintains a temperature of the heating means at 100 to 250° C. and displays an operating status,
   wherein the main body comprises at least one of an angle adjusting unit configured to adjust an angle of the waist plate, an up-and-down adjusting unit configured to adjust a height of the waist plate and a leg unit configured to adjust a height of the sitting plate.

2. The functional chair for human body correction and therapeutic efficacy promotion of claim 1, wherein the sitting plate comprises a plateau which protrudes from a central area of the sitting plate, a circuit board is installed and buried inside the sitting plate and the waist plate comprises a curved surface unit with a specific curvature.

3. The functional chair for human body correction and therapeutic efficacy promotion of claim 1, wherein the heating means comprises a protective pad disposed above or beneath the ceramic heating element, a lagging disposed beneath the ceramic heating element and an insulator disposed above or beneath the ceramic heating element.

4. The functional chair for human body correction and therapeutic efficacy promotion of claim 3, wherein the ceramic heating element comprises:

a ceramic plate including a mixture of kaolin, clay, agalmatolite, feldspar, silica, alumina, and serpentine; and a heating element disposed inside the ceramic plate.

5. The functional chair for human body correction and therapeutic efficacy promotion of claim 1, wherein the ceramic heating element comprises:

a ceramic plate including a mixture of kaolin, clay, agalmatolite, feldspar, silica, alumina, and serpentine; and a heating element disposed inside the ceramic plate.

* * * * *